(12) United States Patent
Tokuda et al.

(10) Patent No.: US 9,150,868 B2
(45) Date of Patent: Oct. 6, 2015

(54) BACTERIUM PRODUCING 2-DEOXY-SCYLLO-INOSOSE (DOI) AND METHOD OF PRODUCING 2-DEOXY-SCYLLO-INOSOSE (DOI) BY USING SAME

(75) Inventors: Junko Tokuda, Chiba (JP); Tomoyuki Natsuji, Mobara (JP); Hitoshi Takahashi, Chiba (JP); Tadashi Araki, Chiba (JP); Takashi Morishige, Mobara (JP); Katsuyuki Takahashi, Singapore (SG); Mitsufumi Wada, Chiba (JP)

(73) Assignee: MITSUI CHEMICALS, INC., Tokyo (JP)

( * ) Notice: Subject to any disclaimer, the term of this patent is extended or adjusted under 35 U.S.C. 154(b) by 398 days.

(21) Appl. No.: 13/126,154

(22) PCT Filed: Oct. 30, 2009

(86) PCT No.: PCT/JP2009/068666
§ 371 (c)(1),
(2), (4) Date: Apr. 26, 2011

(87) PCT Pub. No.: WO2010/053052
PCT Pub. Date: May 14, 2010

(65) Prior Publication Data
US 2011/0207187 A1    Aug. 25, 2011

(30) Foreign Application Priority Data
Nov. 5, 2008 (JP) ................................ 2008-284639

(51) Int. Cl.
*C12P 19/02* (2006.01)
*C12N 15/52* (2006.01)

(52) U.S. Cl.
CPC ............... *C12N 15/52* (2013.01); *C12P 19/02* (2013.01)

(58) Field of Classification Search
CPC .................................................... C12P 19/02
See application file for complete search history.

(56) References Cited

U.S. PATENT DOCUMENTS

| 2001/0049126 A1 | 12/2001 | Livshits et al. |
| 2008/0182308 A1 | 7/2008 | Donaldson et al. |
| 2010/0015672 A1 | 1/2010 | Takagi et al. |

FOREIGN PATENT DOCUMENTS

| EP | 1 149 911 A2 | 10/2001 |
| EP | 1 865 056 A1 | 12/2007 |
| JP | 2000-236881 | 9/2000 |
| JP | 2001-346578 | 12/2001 |
| JP | 2002-512802 | 5/2002 |
| JP | 2006-503559 | 2/2006 |
| WO | WO-99/55877 | 11/1999 |
| WO | WO-2004/033676 A1 | 4/2004 |
| WO | WO-2006/109479 A1 | 10/2006 |
| WO | WO-2006/112000 A1 | 10/2006 |
| WO | WO-2007/041269 A2 | 4/2007 |
| WO | WO-2009/078687 A2 | 6/2009 |

OTHER PUBLICATIONS

International Search Report in PCT/JP2009/068666 dated Dec. 8, 2009.
Jahreis, et al. "Adaptation of Sucrose Metabolism in the *Escherichia coli* Wild-Type Strain EC3132+", Journal of Bacteriology, Oct. 2002, vol. 184, No. 19, pp. 5307-5316.
Kaup, et al. "Metabolic engineering of *Escherichia coli*: construction of an efficient biocatalyst for D-mannitol formation in a whole-cell biotransformation", Appl Microbiol Biotechnol, 2004, vol. 64, pp. 333-339.
Kogure, et al. "Efficient production of 2-deoxy-*scyllo*-inosose from D-glucose by metabolically engineered recombinant *Escherichia coli*", Journal of Biotechnology, 2007, vol. 129, No. 3, pp. 502-509.
Olson, et al. "Production of tyrosine from sucrose or glucose achieved by rapid genetic changes to phenylalanine-producing *Escherichia coli* strains", Appl Microbiol Biotechnol, 2007, vol. 74, pp. 1031-1040.
Sahin-Toth, et al. "Cloning, sequencing, and expression of cscA invertase from *Escherichia coli* B-62", Can. J. Microbiol, 1999, vol. 45, pp. 418-422.
Shukla, et al. "Production of D(-)-lactate from sucrose and molasses", Biotechnology Letters, 2004, vol. 26, pp. 689-293.
Sproul, et al. "Genetic control of manno(fructo)kinase activity in *Escherichia coli*", PNAS, Dec. 18, 2001, vol. 98, No. 26, pp. 15257-15259.
Voronovsky, et al. "Expression of xy/A genes encoding xylose isomerases from *Escherichia coli* and *Streptomyces coelicolor* in the methylotrophic yeast *Hansenula polymorpha*", FEMS Yeast Research, 2005, vol. 5, pp. 1055-1062.

*Primary Examiner* — Rebecca Prouty
(74) *Attorney, Agent, or Firm* — Foley & Lardner LLP

(57) ABSTRACT

Disclosed is an *Escherichia coli* producing 2-deoxy-scyllo-inosose (DOI), which, from a sucrose non-PTS gene group, has at least a sucrose hydrolase (CscA)-encoding gene and which is provided with a DOI production system or has an enhanced DOI production system. The *Escherichia coli* preferably further includes a system to enhance sugar uptake capacity. There is also disclosed a method of producing DOI from a plant-derived raw material containing sucrose by using the *Escherichia coli*.

6 Claims, 1 Drawing Sheet

SEQUENCE LISTING

<160> NUMBER OF SEQ ID NOS: 18

<210> SEQ ID NO 1
<211> LENGTH: 29
<212> TYPE: DNA
<213> ORGANISM: Artificial
<220> FEATURE:
<223> OTHER INFORMATION: primer1

<400> SEQUENCE: 1
caggaattcg ctatatctgg ctctgcacg                                29

<210> SEQ ID NO 2
<211> LENGTH: 31
<212> TYPE: DNA
<213> ORGANISM: Artificial
<220> FEATURE:
<223> OTHER INFORMATION: primer2

<400> SEQUENCE: 2
cagtctagag caatactctt ctgattttga g                             31

<210> SEQ ID NO 3
<211> LENGTH: 29
<212> TYPE: DNA
<213> ORGANISM: Artificial
<220> FEATURE:
<223> OTHER INFORMATION: primer3

<400> SEQUENCE: 3
cagtctagat catcgtcgat atgtaggcc                                29

<210> SEQ ID NO 4
<211> LENGTH: 29
<212> TYPE: DNA
<213> ORGANISM: Artificial
<220> FEATURE:
<223> OTHER INFORMATION: primer4

<400> SEQUENCE: 4
gacctgcaga tcatccgtca gctgtacgc                                29

<210> SEQ ID NO 5
<211> LENGTH: 29
<212> TYPE: DNA
<213> ORGANISM: Artificial
<220> FEATURE:
<223> OTHER INFORMATION: primer5

<400> SEQUENCE: 5
caggaattca tgcgttgcag cacgatatc                                29

<210> SEQ ID NO 6
<211> LENGTH: 29
<212> TYPE: DNA
<213> ORGANISM: Artificial
<220> FEATURE:
<223> OTHER INFORMATION: primer6

<400> SEQUENCE: 6
cagtctagat aacccggtac ttaagccag                                29

<210> SEQ ID NO 7
<211> LENGTH: 29
<212> TYPE: DNA
<213> ORGANISM: Artificial

```
<220> FEATURE:
<223> OTHER INFORMATION: primer7

<400> SEQUENCE: 7
cagtctagac tgcgcttatc ctttatggt                              29

<210> SEQ ID NO 8
<211> LENGTH: 29
<212> TYPE: DNA
<213> ORGANISM: Artificial
<220> FEATURE:
<223> OTHER INFORMATION: primer8

<400> SEQUENCE: 8
gacctgcagt taccggtcat gcgtgtaac                              29

<210> SEQ ID NO 9
<211> LENGTH: 33
<212> TYPE: DNA
<213> ORGANISM: Artificial
<220> FEATURE:
<223> OTHER INFORMATION: primer9

<400> SEQUENCE: 9
cgagctacat atgcaatgat tgacacgatt ccg                         33

<210> SEQ ID NO 10
<211> LENGTH: 56
<212> TYPE: DNA
<213> ORGANISM: Artificial
<220> FEATURE:
<223> OTHER INFORMATION: primer10

<400> SEQUENCE: 10
ccaagcttct gcaggtcgac ggatccgagc tcagctattt gttagtgaat aaaagg    56

<210> SEQ ID NO 11
<211> LENGTH: 44
<212> TYPE: DNA
<213> ORGANISM: Artificial
<220> FEATURE:
<223> OTHER INFORMATION: primer11

<400> SEQUENCE: 11
cactggagct cgctggtgga atatatgacg actaaacaaa tttg             44

<210> SEQ ID NO 12
<211> LENGTH: 27
<212> TYPE: DNA
<213> ORGANISM: Artificial
<220> FEATURE:
<223> OTHER INFORMATION: primer12

<400> SEQUENCE: 12
caggatcctt acagcccttc ccggatc                                27

<210> SEQ ID NO 13
<211> LENGTH: 40
<212> TYPE: DNA
<213> ORGANISM: Artificial
<220> FEATURE:
<223> OTHER INFORMATION: primer13

<400> SEQUENCE: 13
gcggatccgc tggtggaata tatgacgcaa tctcgattgc                  40
```

```
<210> SEQ ID NO 14
<211> LENGTH: 32
<212> TYPE: DNA
<213> ORGANISM: Artificial
<220> FEATURE:
<223> OTHER INFORMATION: primer14

<400> SEQUENCE: 14
gacgcgtcga cttaacccag ttgccagagt gc                            32

<210> SEQ ID NO 15
<211> LENGTH: 44
<212> TYPE: DNA
<213> ORGANISM: Artificial
<220> FEATURE:
<223> OTHER INFORMATION: primer15

<400> SEQUENCE: 15
cctgtcgacg ctggtggaat atatgagttc tgaaagtagt cagg              44

<210> SEQ ID NO 16
<211> LENGTH: 29
<212> TYPE: DNA
<213> ORGANISM: Artificial
<220> FEATURE:
<223> OTHER INFORMATION: primer16

<400> SEQUENCE: 16
ctactgcagc tacttctggg agcgccaca                                29

<210> SEQ ID NO 17
<211> LENGTH: 43
<212> TYPE: DNA
<213> ORGANISM: Artificial
<220> FEATURE:
<223> OTHER INFORMATION: primer17

<400> SEQUENCE: 17
tactgcagag ctggtggaat atatgcgcgt taacaatggt ttg               43

<210> SEQ ID NO 18
<211> LENGTH: 28
<212> TYPE: DNA
<213> ORGANISM: Artificial
<220> FEATURE:
<223> OTHER INFORMATION: primer18

<400> SEQUENCE: 18
tactgcagtt acagtttcgg accagccg                                 28
```

BACTERIUM PRODUCING 2-DEOXY-SCYLLO-INOSOSE (DOI) AND METHOD OF PRODUCING 2-DEOXY-SCYLLO-INOSOSE (DOI) BY USING SAME

TECHNICAL FIELD

The present invention relates to a bacterium that produces 2-deoxy-scyllo-inosose (DOI) from sucrose and a method of producing DOI using the same.

BACKGROUND ART 2-deoxy-scyllo-inosose (hereinafter also referred to as DOI) is a useful substance used as a pharmaceutical raw material and a chemical industry resource. For example, according to Japanese Patent Application Laid-Open (JP-A) No. 2000-236881, it is shown that 2-deoxy-scyllo-inosose can be produced from glucose-6-phosphate (G-6-P) through a short process using a recombinant DOI synthase obtained using *Escherichia coli*. Furthermore, for example, according to International Publication (WO) No. 2006/109479, a method of producing DOI from glucose in a single step by using *Escherichia coli* expressing a DOI synthase has been developed. This has enabled the production of DOI from glucose obtained from a plant-derived resource.

However, according to the Journal of Biotechnology, Vol. 129, pp. 502-509 (2007), it has been found that the DOI production method described in WO No. 2006/109479 not only uses glucose as the raw material but also separately requires mannitol, which is a rare and expensive sugar, for the proliferation and growth of the bacterial cell. In the above Journal, it has been shown that simple expression of the DOI synthase in a wild type *Escherichia coli* produces only 1.5 g/L of DOI, and to achieve high productivity (29.5 g/L), it is necessary to simultaneously disrupt three enzyme genes present in *Escherichia coli*; namely, phosphoglucose isomerase (pgi), glucose-6-phosphate-1-dehydrogenase (zwf), and phosphoglucomutase (pgm). Thus, it has been concluded that since all the metabolic pathways through which glucose enters the glycolytic pathway are blocked, a sugar (such as mannitol) that is separately usable in the glycolytic pathway is required for the proliferation and growth of the bacterial cell. In addition, to obtain similar high productivity of DOI, it may be enough to merely simultaneously disrupt the two genes pgi and zwf. However, even in this case, it is clear that when glucose is the only carbon source, the bacterial cell cannot proliferate, so that mannitol remains necessary for the proliferation and growth thereof.

Meanwhile, sucrose is known as a sugar raw material that is less expensive than glucose. Sucrose is a main component of blackstrap molasses. It is expected that *Escherichia coli* producing DOI by assimilating sucrose will be useful in the production of inexpensive DOI that is useful for industrial purposes, although to date no bacteria have existed that produce DOI by sucrose assimilation.

For example, in JP-A No. 2001-346578, the mechanism of sucrose assimilation in a microorganism is roughly classified into two systems: the sucrose PTS (Phosphoenolpyruvate: Carbohydrate Phosphotransferase System) and the sucrose non-PTS. In the case of assimilation through the sucrose non-PTS, the microorganism incorporates sucrose as it is and decomposes it into glucose and fructose. On the other hand, in assimilation through the sucrose PTS, the microorganism incorporates sucrose by means of phosphorylation of sucrose to convert it to sucrose-6-phosphate, and then decomposes it into glucose-6-phosphate and fructose within itself.

In other words, through either mechanism, sucrose-derived fructose appears in the microorganism, first in its non-phosphorylated form. Then, to allow fructose that is not phosphorylated (hereinafter referred to as non-phosphorylated fructose) to be taken into the glycolytic pathway, fructose needs to be isomerized into glucose or phosphorylated. However, FEMS Yeast Research, Vol. 5, pp. 1055-1062 (2005), Proceedings of the National Academy of Sciences of the United States of America (PNAS), Vol. 98(26), pp. 15257-15259 (2001), and the Journal of Bacteriology, Vol. 184(19), pp. 5307-5316 (2002) have suggested that when the microorganism is *Escherichia coli*, the activity of isomerizing non-phosphorylated fructose into glucose and the activity of phosphorylating fructose are both extremely low. Therefore, even if non-phosphorylated fructose successfully appears in *Escherichia coli*, it has not been expected that *Escherichia coli* will assimilate the non-phosphorylated fructose unless other means is provided.

The Canadian Journal of Microbiology, Vol. 45, pp. 418-422 (1999) has disclosed that introducing only a sucrose hydrolase gene (cscA) into *Escherichia coli* has enabled the proliferation of *Escherichia coli* with sucrose as a raw material. On the other hand, one important thing in DOI production by *Escherichia coli* using sucrose as a raw material is that the bacterial cell proliferation and growth is achieved by using sucrose-derived fructose. However, the above literature has disclosed consistently only information regarding the introduction of sucrose and glucose into the bacterial cell, and has not disclosed any data on the extent of assimilation of sucrose-derived fructose.

SUMMARY OF THE INVENTION

Technical Problem

As described above, the conventionally known DOI-producing *Escherichia coli* have been problematic in industrial production of DOI, since glucose has been required for DOI production and, further, the expensive sugar, mannitol or the like has been required for bacterial cell proliferation.

Accordingly, it is an object of the present invention to provide an *Escherichia coli* capable of efficiently producing DOI from the inexpensive sugar sucrose, and a method of producing DOI using the bacterium.

Solution to Problem

The present invention has been accomplished in view of the above circumstances. The following are the DOI-producing *Escherichia coli* and the DOI-production method according to the present invention.

[1] An *Escherichia coli* producing 2-deoxy-scyllo-inosose (DOI), which, from a sucrose non-PTS gene group, has at least a sucrose hydrolase (CscA)-encoding gene and which is provided with a DOI production system or has an enhanced DOI production system.

[2] The DOI-producing *Escherichia coli* according to [1], which has only the sucrose hydrolase (CscA)-encoding gene from the sucrose non-PTS gene group.

[3] The DOI-producing *Escherichia coli* according to [1] or [2], which has a system to enhance sugar uptake capacity.

[4] The DOI-producing *Escherichia coli* according to [3], wherein the activity of at least one selected from the group consisting of phosphoglucose isomerase (Pgi), glucose-6-phosphate-1-dehydrogenase (Zwf), phosphoglucomutase (Pgm), and a ribosome modulation factor (Rmf) involved in modulation of protein synthesis in a stationary phase, which are inherent in the *Escherichia coli*, is inactivated or reduced.

[5] The DOI-producing *Escherichia coli* according to any one of [1] to [4], wherein the DOI production system is derived from DOI synthase (BtrC) activity.

[6] The DOI-producing *Escherichia coli* according to any one of [3] to [5], wherein the system to enhance the sugar uptake capacity comprises enhancement of glucose transport facilitator (Glf) activity.

[7] The DOI-producing *Escherichia coli* according to any one of [1] to [6], wherein the sucrose hydrolase (CscA)-encoding gene is derived from *Escherichia coli* bacteria.

[8] The DOI-producing *Escherichia coli* according to [7], wherein the *Escherichia coli* bacteria is *Escherichia coli* O157 bacteria.

[9] The DOI-producing *Escherichia coli* according to any one of [6] to [8], wherein the glucose transport facilitator (Glf) is derived from bacteria belonging to the genus *Zymomonas*.

[10] The DOI-producing *Escherichia coli* according to [9], wherein the bacteria belonging to the genus *Zymomonas* is *Zymomonas mobilis* bacteria.

[11] The DOI-producing *Escherichia coli* according to any one of [1] to [10], which is a kind of *Escherichia coli* that inherently lacks an ability to assimilate sucrose.

[12] The DOI-producing *Escherichia coli* according to [11], which is a B strain or a derivative thereof.

[13] A method of producing DOI, which comprises producing DOI from a plant-derived raw material containing sucrose by using the DOI-producing *Escherichia coli* according to any one of [1] to [12].

Advantageous Effects of Invention

The present invention can provide a DOI-producing *Escherichia coli* that efficiently produces DOI from sucrose as the only carbon source, and a method of producing DOI by using the bacterium.

DESCRIPTION OF EMBODIMENTS

Figure 1:
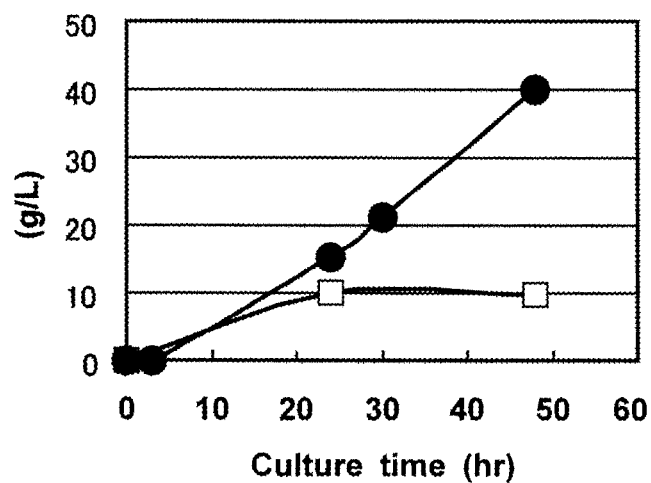
FIG. 1 shows a chart indicating the DOI productivities of bacterial strains obtained in Example 11 of the present invention.

The *Escherichia coli* producing 2-deoxy-scyllo-inosose (DOI) according to the present invention is a DOI-producing *Escherichia coli* that has at least a sucrose hydrolase (CscA)-encoding gene from a sucrose non-PTS gene group and is provided with a DOI production system or has an enhanced DOI production system.

The present invention has discovered that DOI can be produced extremely efficiently from sucrose as the only carbon source by having sucrose-derived fructose assimilated by a DOI-producing *Escherichia coli* that has at least a sucrose hydrolase (CscA)-encoding gene from a sucrose non-PTS gene group and that is provided with a DOI production system or has an enhanced DOI production system. As a result, DOI can be efficiently obtained from plant-derived sucrose that is inexpensive and common in industrial use.

Specifically, the DOI-producing *Escherichia coli* according to the present invention can phosphorylate sucrose-derived fructose to introduce it into the bacterial cell, and can convert the fructose to energy for the proliferation and growth of the bacterial cell via the glycolytic pathway. There have been no reported cases to date of DOI production by an *Escherichia coli* using sucrose-derived fructose as a nutritional source for bacterial cell proliferation as described above.

To explain in more detail, the sucrose hydrolase (CscA) is recognized as an enzyme that hardly exists on the cell membrane of *Escherichia coli* (see the Canadian Journal of Microbiology, Vol. 45, pp. 18-422 (1999)). Meanwhile a DOI-producing *Escherichia coli* is formulated so as to be incapable of incorporating non-phosphorylated fructose into the glycolytic pathway and capable of using only phosphorylated fructose for its growth (see WO No. 2006/109479). The present invention has introduced, into such a DOI-producing *Escherichia coli*, at least the sucrose hydrolase (CscA)-encoding gene from the sucrose non-PTS gene group to provide CscA activity. As a result, greatly contrary to expectations, the invention has obtained a DOI-producing *Escherichia coli* capable of using fructose as a nutritional source. The DOI-producing *Escherichia coli* of the present invention thus obtained can produce DOI by efficiently assimilating sucrose and fructose as a sucrose decomposition product, regardless of the presence of glucose that is the easiest sugar for an *Escherichia coli* to use. Thus, DOI production can be accomplished regardless of the reduction or depletion of glucose, whereby DOI can be more efficiently produced. By the decomposition of sucrose, glucose and fructose are produced in equivalent amounts. However, it is generally known that, usually in an *Escherichia coli*, glucose uptake precedes fructose uptake and thus fructose is not sufficiently metabolized in the presence of glucose. Accordingly, it is surprising that, for example, by adjusting the pH in the bacterial cell culture, fructose has been able to be efficiently used for the growth of the *Escherichia coli* without any influence of metabolism inhibition (catabolite repression) by glucose.

Hereinafter, a detailed explanation will be given of the present invention.

In the present specification, the range of numerical values indicated by "to" shows a range including the numerical values described before and after the "to", as the minimum value and the maximum value, respectively.

In the present invention, "sucrose assimilation" means an ability to effect in vivo uptake of sucrose as it is or after modification of sucrose into a low-molecular weight counterpart thereof or a high-molecular weight counterpart thereof, preferably a low-molecular weight counterpart thereof, or an ability to metabolically convert sucrose to another substance. Additionally, assimilation in the present invention includes decomposition in which sucrose is modified into a low-molecular weight counterpart thereof, and specifically includes decomposition of sucrose into D-glucose and D-fructose.

In the present invention, "sucrose non-PTS gene group" means a gene group involved in a non-PTS system from a sucrose assimilation pathways of microorganisms. Specifically, the gene group includes a gene (cscR) encoding a repressor protein (CscR), a gene (cscA) encoding a sucrose hydrolase (CscA), a gene (cscK) encoding a fructokinase (CscK), and a gene (cscB) encoding a sucrose permease (CscB). From them, the present invention only needs to include at least the cscA. For example, there may be mentioned the cscA alone, the combination of the cscA and the cscK, the combination of the cscA and the cscB, the combination of the cscA and the cscR, the combination of the cscA, the cscB, and the cscR, the combination of the cscA, the cscK, and the cscR, the combination of the cscA, the cscK, and the cscB, or the combination of the cscA, the cscK, the cscB, and the cscR.

Above all, it is preferable to include the cscA alone, without the other genes, in the light of more efficient production of DOI.

In the present invention, "sucrose hydrolase (CscA)" represents a generic term for enzymes that are classified with the enzyme code number 3.2.1.26 based on the report of the commission on enzymes of the International Union of Biochemistry (I.U.B) and catalyze a reaction for producing D-glucose and D-fructose from sucrose. *Escherichia coli* strains, such as K-12 and B, inherently lack the enzyme.

In the present invention, due to the introduction of at least the cscA from the sucrose non-PTS gene group into the *Escherichia coli* to provide the CscA activity and, in particular, due to the introduction of only the cscA from the sucrose non-PTS gene group into the *Escherichia coli* to provide only the CscA activity, sucrose existing outside the bacterial cell is decomposed into glucose and fructose on the cell membrane, which are released out of the cell. Then, they are incorporated into the cytoplasm by being phosphorylated through a glucose PTS and a fructose PTS that are inherent in the *Escherichia coli*. As a result, the extracellular fructose appears as fructose-1-phosphate in the bacterial cell and is then converted to fructose-1,6-phosphate by fructose-1-phosphate kinase (FruK) existing in the bacterial cell, and taken into the glycolytic pathway.

As the gene (cscA) of the sucrose hydrolase (CscA) that can be introduced into a host bacterium of the present invention, a DNA obtained from an organism possessing the enzyme can be used that has the base sequence of a gene encoding the sucrose hydrolase (CscA), or a synthetic DNA can be used that synthesized based on its known base sequence. Preferred are genes derived from the genus *Erwinia*, the genus *Proteus*, the genus *Vibrio*, the genus *Agrobacterium*, the genus *Rhizobium*, the genus *Staphylococcus*, the genus *Bifidobacterium*, and the genus *Escherichia*. For example, there can be exemplified a DNA that has the base sequence of the gene derived from an *Escherichia coli* O157 stain. Particularly preferred is a DNA that has the base sequence of an *Escherichia coli* O157 strain-derived gene. In addition, preferably, to the cscA is added a signal sequence for transporting the CscA into the bacterial periplasm.

As the gene of the repressor protein (CscR) that can be introduced into a host bacterium of the present invention, a DNA obtained from an organism possessing the enzyme can be used that has the base sequence of a gene encoding the repressor protein (CscR), or a synthetic DNA can be used that synthesized based on its known base sequence. Preferred are genes derived from the genus *Erwinia*, the genus *Proteus*, the genus *Vibrio*, the genus *Agrobacterium*, the genus *Rhizobium*, the genus *Staphylococcus*, the genus *Bifidobacterium*, and the genus *Escherichia*. For example, there can be exemplified a DNA that has the base sequence of the gene derived from an *Escherichia coli* O157 strain. Particularly preferred is a DNA that has the base sequence of an *Escherichia coli* O157 strain-derived gene.

As the gene of the fructokinase (CscK) that can be introduced into a host bacterium of the present invention, a DNA obtained from an organism possessing the enzyme can be used that has the base sequence of a gene encoding the fructokinase (CscK), or a synthetic DNA can be used that synthesized based on its known base sequence. Preferred are genes derived from the genus *Erwinia*, the genus *Proteus*, the genus *Vibrio*, the genus *Agrobacterium*, the genus *Rhizobium*, the genus *Staphylococcus*, the genus *Bifidobacterium*, and the genus *Escherichia*. For example, there can be exemplified a DNA that has the base sequence of the gene derived from an *Escherichia coli* O157 strain. Particularly preferred is a DNA that has the base sequence of an *Escherichia coli* O157-derived gene.

As the gene of the sucrose permease (CscB) that can be introduced into a host bacterium of the present invention, a DNA obtained from an organism possessing the enzyme can be used that has the base sequence of a gene encoding the sucrose permease (CscB), or a synthetic DNA can be used that synthesized based on its known base sequence. Preferred are genes derived from the genus *Erwinia*, the genus *Proteus*, the genus *Vibrio*, the genus *Agrobacterium*, the genus *Rhizobium*, the genus *Staphylococcus*, the genus *Bifidobacterium*, and the genus *Escherichia*. For example, there can be exemplified a DNA that has the base sequence of the gene derived from an *Escherichia coli* O157 strain. Particularly preferred is a DNA that has the base sequence of an *Escherichia coli* O157-derived gene.

In the present invention, "host bacterium" means an *Escherichia coli* that becomes the DOI-producing *Escherichia coli* of the present invention obtained as the result of the introduction of one or more genes from outside the bacterial cell.

In the present invention, "DOI production system" represents a structure of providing a DOI production ability introduced or modified by genetic recombination. Such a DOI production system can be any as long as it increases the amount of DOI production by *Escherichia coli* as target.

Preferably, there can be mentioned provision or enhancement, or the combination thereof, of enzyme activity associated with DOI production. Thereby, with a combination with the above CscA activity, DOI can be effectively produced from sucrose, even by an *Escherichia coli* that inherently lacks an ability to assimilate sucrose.

In the present invention, "provision" or "enhancement" includes, other than an introduction of an enzyme-encoding gene into a host bacterium from thereoutside, an enhancement of promoter activity of an enzyme-encoding gene present on the genome of a host bacterium or a strong expression of an enzyme-encoding gene by replacement with another promoter.

The phrase "by genetic recombination" in the present invention includes any one as long as it leads to change(s) on the base sequence of a gene by an insertion of another DNA into the inherent base sequence, or a substitution or deletion of a certain site of a gene, or a combination thereof. For example, it may be one obtained as a result of mutation.

The DOI production system in the present invention is preferably derived from a DOI synthase (BtrC) activity in the light of DOI production efficiency. Such a DOI synthase can be provided in the *Escherichia coli* by introducing a DOI synthase gene (btrC) thereinto.

The DOI synthase (BtrC) is an enzyme that catalyzes a production of 2-deoxy-scyllo-inosose (DOI) from glucose-6-phosphate. It is known that the DOI synthase is a dimer consisting of a 42 kDa peptide and a 23 kDa peptide; the enzyme activity is promoted in the presence of cobalt ions and inhibited in the presence of zinc and copper ions, as well as the enzyme reaction is driven by a coenzyme $NAD^+$ (for example, see JP-A No. 2000-236881 and WO No. 2006/109479). Any btrC gene can be used as long as it is derived from an organism having the gene, and for example, there may be mentioned the btrC gene derived from the genus *Bacillus*. In the light of DOI production efficiency, a preferable btrC gene to be used is a gene encoding a 42 kDa subunit derived from *Bacillus circulans* (GenBank accession number AB066276).

The DOI-producing *Escherichia coli* according to the present invention preferably has a system to enhance sugar uptake capacity.

Sugar uptake capacity in the present invention means the capacity to transport sugar through biomembrane, where the capacity can include action for either of sugar transport from outside to inside of biomembrane or sugar transport from inside to outside thereof. Examples of sugar in sugar transport include 5 monosaccharides or 6 monosaccharides. Specifically, there may be mentioned glucose, mannose, arabinose, galactose, fructose, and the like. Preferred is glucose.

In the present invention, the phrase "having a system to enhance sugar uptake capacity" shows a state in which sugar uptake from outside to inside of a bacterial cell has increased. In the present invention, "a system to enhance sugar uptake capacity" preferably means a structure of improving an activity to incorporate glucose. More preferably, the system to enhance the sugar uptake capacity is different from the PTS system or the non-PTS system and is, for example, a system for incorporating glucose outside a bacterial cell thereinto in its original form. Incorporated glucose is then phosphorylated by a phosphatase such as glucokinase (Glk) inherent in a bacterial cell to be used as a substrate for use in substance production. Thereby, *Escherichia coli* acquires a new sugar uptake system, other than a sugar uptake system inherently present therein as the PTS system or the non-PTS system.

The system to enhance the sugar uptake capacity in the present invention is preferably a system to enhance a glucose transport facilitator (Glf) activity in the light of DOI production efficiency.

Glucose transport facilitator (Glf) in the present invention represents a general term for proteins serving to transport D-glucose, D-fructose, and the like from outside to inside of biomembrane. There are known the techniques for improving the productivity of mannitol (for example, see JP-T-2006-503559) and the improved productivity of L-phenylalanine and shikimic acid (for example, see JP-T-2002-512802 and Applied Microbiology and Biotechnology (2004) 64, 333-339) in *Escherichia coli* into which the glf gene has been introduced. However, it was not known at all as to whether an introduction of a glucose transport facilitator gene (glf) had an effect of improving DOI productivity even on a DOI-producing *Escherichia coli*. Meanwhile, as will be described below, an introduction of a glf gene is not effective in improving productivity of lactic acid. Accordingly, an introduction of a glf gene is not a commonly effective technique in substance productions using sugar as a raw material. Therefore, it is surprising that the present invention has enabled DOI to be efficiently produced by introducing the glf gene.

As the glucose transport facilitator gene (glf) to be introduced into a host bacterium of the present invention, a DNA obtained from an organism possessing the enzyme can be used that has the base sequence of a gene encoding the glucose transport facilitator (Glf), or a synthetic DNA can be used that synthesized based on its known base sequence. Preferably, there may be mentioned genes derived from yeast or the genus *Zymomonas*, and more preferably, derived from the genus *Zymomonas*. For example, there can be exemplified a DNA that has the base sequence of a gene derived from *Zymomonas mobilis*. Particularly preferred is a DNA that has the base sequence of a *Zymomonas mobilis*-derived gene.

A DOI-producing *Escherichia coli* according to a more preferable aspect of the present invention can be a DOI-producing *Escherichia coli* in which the sucrose hydrolase (CscA) activity is obtained by an introduction of a gene encoding the protein derived from the genus *Escherichia* in the light of ability to decompose sucrose, and the glucose transport facilitator (Glf) activity is obtained by an introduction of a gene encoding the protein derived from the genus *Zymomonas* in the light of DOI productivity improvement. More preferably, the sucrose hydrolase (CscA) is obtained by an introduction of a gene encoding the protein derived from *Escherichia coli* O157, and the glucose transport facilitator (Glf) is obtained by an introduction of a gene encoding the protein derived from *Zymomonas mobilis*. Using the genes derived from those bacteria can ensure the expression of functions of the genes.

A promoter for expressing each gene in the present invention can be any promoter, as long as it can control the expression of any of the above-described genes. Preferred is a promoter that is powerful enough to constantly function in the microorganism and scarcely restrained from expressing even in the presence of glucose. Specifically, there can be exemplified a promoter of glyceraldehyde-3-phosphate dehydrogenase (hereinafter may be referred to as GAPDH) and a promoter of serine hydroxymethyltransferase.

In the present invention, *Escherichia coli* provided with each activity represents *Escherichia coli* in which each enzyme or protein-based activity has been provided from outside to inside of the bacterium by means of a certain method. Such an *Escherichia coli* as above can be prepared, for example by a method such as introduction of gene(s) encoding enzyme(s) or protein(s) from outside to inside of the bacterium by using a genetic recombination technique. Genomic DNA preparation, breakage and binding of DNA, transformation, PCR (Polymerase Chain Reaction), design and synthesis of oligonucleotides used as primers, and the like, which are necessary for introduction of gene(s) from outside to inside of the bacterium, can be carried out by usual methods well-known to those skilled in the art. Those methods are described in "Molecular Cloning: A Laboratory Manual (Second Edition)" by Sambrook, J. et al., (Cold Spring Harbor Laboratory Press (1989)), and the like.

According to a preferable aspect of the present invention, to produce DOI in as high yield as possible, the activity of at least one selected from the group consisting of the following enzymes involved in the metabolism of glucose-6-phosphate inherent in a host bacterium, namely, phosphoglucose isomerase (Pgi), glucose-6-phosphate-1-dehydrogenase (Zwf), and phosphoglucomutase (Pgm), and a ribosome modulation factor (Rmf) involved in modulation of protein synthesis in a stationary phase is inactivated or reduced. In such an aspect of the invention, each gene encoding each of the above enzymes (each of the pgi gene, the zwf gene, and the pgm gene) is exclusively disrupted, two of the genes (the pgi gene and the zwf gene, or the pgi gene and the pgm gene) are simultaneously disrupted, or the three genes are simultaneously disrupted, and the rmf gene encoding the RMF protein involved in control of protein synthesis in the stationary phase is exclusively disrupted or the rmf gene is disrupted in various gene-disrupted strains in which the above genes involved in the metabolism of glucose-6-phosphate have been disrupted.

This inhibits the decomposition and metabolism, by the bacterium, of glucose-6-phosphate serving as a direct substrate for DOI production, and protein synthesis in the stationary phase allows for improvement in the ability to produce DOI. The DOI-producing bacterium as described above is described, for example, in the pamphlet WO No. 2006/109479.

The DOI-producing *Escherichia coli* according to the present invention is more preferably an *Escherichia coli* in which activities of phosphoglucose isomerase (Pgi) and glucose-6-phosphate-1-dehydrogenase (Zwf) have been simultaneously inactivated or reduced. Most preferred is an *Escherichia coli* in which activities of phosphoglucose isomerase (Pgi), glucose-6-phosphate-1-dehydrogenase (Zwf), and phosphoglucomutase (Pgm) have been simultaneously inactivated or reduced.

Any means for inactivating various enzymes can be used without specific limitation as long as it is a means usually used for that purpose, and for example, there can be mentioned gene disruption by homologous recombination of genes encoding the enzymes or the like. Such a gene disruption may be a disruption of a chromosomal gene or a plasmid gene.

In addition, the *Escherichia coli* of the present invention to be used may be a strain in which various chromosomal/plasmid genes have been disrupted in consideration of DOI synthesis.

In the present invention, "inactivation" represents a state in which activity of the corresponding enzyme measured by an existing measurement system is no more than a detection limit.

In the present invention, "reduction" represents a state in which, due to genetic recombination of an enzyme-encoding gene, activity of the corresponding enzyme is extremely lower than a state before the process thereof.

Enzyme activity in the present invention may be activity measured by any existing measurement system.

In the present invention, "gene disruption" means that, to render a specific gene non-functional, a mutation is introduced into the base sequence of the gene, another DNA is inserted into the base sequence of the gene, or a certain site of the gene is deleted. As the result of gene disruption, the gene cannot be transcribed into mRNA and thus, the structural gene is not translated, or the transcribed mRNA is incomplete and thus, mutation or deletion occurs in the amino acid sequence of the translated structural protein, thereby preventing the protein from exerting its inherent function.

For the construction of a gene-disrupted strain, any technique can be used, as long as it can prepare a gene-disrupted strain that does not express the corresponding enzyme or protein. Regarding the gene disruption technique, there have been reported various techniques (natural breeding, mutagen addition, ultraviolet irradiation, radiation exposure, random mutagenesis, transposon mutagenesis, and site-specific gene disruption). Preferred is gene disruption by homologous recombination, since it can disrupt only a specific gene. Techniques using homologous recombination have been described in the Journal of Bacteriology, 161, 1219-1221 (1985), the Journal of Bacteriology, 177, 1511-1519 (1995), and PNAS, 97, 6640-6645 (2000). With those methods and applications thereof, the homologous recombination can be easily implemented by those skilled in the art.

*Escherichia coli* to be used in the present invention can be any, as long as it enables the introduction and modification of the above individual genes. More preferred are the kinds of *Escherichia coli* that inherently lack an ability to assimilate sucrose. A suitably used kind is *Escherichia coli* that provides particularly high convenience and has long been used for numerous industrial purposes. For example, there may be mentioned the K-12 strain, the B strain, the C strain, and derivatives thereof. Using them can increase the range of uses for the kinds of *Escherichia coli* that inherently lack an ability to assimilate sucrose.

Among the kinds of *Escherichia coli* that inherently lack an ability to assimilate sucrose, the B strain and its derivative strain are suitably used as the DOI-producing *Escherichia coli* of the present invention. By constructing the DOI-producing *Escherichia coli* of the present invention by using the B strain and its derivative strain, high DOI productivity can be achieved with corn steep liquor, which is a general-purpose industrial culture medium. *Escherichia coli* is generally classified into the strains of K-12, B, and C. As host bacteria for industrial substance production, K-12 and B derivative strains are widely used. Both kinds of strains allow for the expression of heterogeneous proteins by genetic recombination, although it has not been known at all that the B strain is a preferable host for DOI production. Therefore, it is an unpredictable, specific phenomenon that the B derivative strains showed extremely higher productivity than the K-12 derivative strains in DOI production.

The method of producing DOI according to the present invention includes producing 2-deoxy-scyllo-inosose from a plant-derived raw material containing sucrose by using the DOI-producing *Escherichia coli* described above. Specifically, the method includes a step of bringing the DOI-producing *Escherichia coli* into contact with the plant-derived raw material containing sucrose and a step of collecting DOI obtained by the contact.

In the present specification, the term "step" includes not only an independent step but also even a step that cannot be clearly distinguished from any other step as long as the step can achieve its expected operation.

The plant-derived raw material used in the above DOI production method is a carbon source obtained from a plant and is not specifically limited as long as it can be metabolized by the *Escherichia coli* to be converted to DOI. In the present invention, plant-derived raw material represents organs such as roots, stalks, stems, branches, leaves, flowers, and seeds, plant bodies including them, and decomposition products of the plant organs, as well as includes raw materials that can be used as carbon sources by microorganisms in culture, among carbon sources obtained from the plant bodies, the plant organs, or the decomposition products thereof.

As carbon sources included in the plant-derived raw materials, besides sucrose, there can be generally exemplified saccharides such as starch, glucose, fructose, xylose, and arabinose, or the decomposition products of herbaceous and ligneous plants and cellulose hydrolysate that contain those ingredients in large amounts, and the like. Furthermore, vegetable oil-derived glycerin and fatty acids are also applicable to the carbon source used in the present invention.

Preferable examples of plant-derived raw material in the present invention can include crops such as grain, corn, wheat, soybean, sugarcane, beet, cotton, and the like, or combinations thereof. The form of them to be used as the raw material is not specifically limited and they may be in the form of a crude product, squeezed juice, the product of crushed particles, or the like. Alternatively, the plant-derived raw material may be used only in the form of the carbon sources mentioned above.

At the contact step, the DOI-producing *Escherichia coli* is brought into contact with a plant-derived raw material, generally by culturing the DOI-producing *Escherichia coli* in a culture medium containing a plant-derived raw material.

The contact density between a plant-derived raw material and the DOI-producing *Escherichia coli* varies depending on the activity of the DOI-producing *Escherichia coli*. In general, as the concentration of a plant-derived raw material in the culture medium, the initial sugar concentration in terms of glucose can be 20% by mass or lower relative to the total mass of a mixture. In the light of the sugar tolerance of the *Escherichia coli*, preferably, the initial sugar concentration can be 15% by mass or lower. Other individual components can be added in amounts thereof usually added in culture media for microorganisms, and the addition amounts thereof are not specifically limited.

The content of the DOI-producing *Escherichia coli* in the culture medium varies depending on the kind and activity of the *Escherichia coli*. In general, the initial concentration of the *Escherichia coli* relative to the culture solution can be set in a range from 0.1% by mass to 30% by mass, and in the light of culture condition control, preferably, it can be set in a range from 1% by mass to 10% by mass.

The DOI production method according to the present invention includes a method in which a plant-derived raw material is assimilated by culturing the DOI-producing *Escherichia coli* in a mixture containing the DOI-producing *Escherichia coli* and a plant-derived raw material to purify DOI secreted in the culture solution after elapse of a certain time by using well-known techniques such as distillation, membrane separation, and extraction. The mixture to be used in the DOI production method can be any as long as it is mainly composed of a basal medium commonly used in bacteria culture and as long as it is a culture medium usually used in accordance with the kind of the DOI-producing *Escherichia coli*. Such a basal medium is not specifically limited as long as it contains a carbon source, a nitrogen source, an inorganic ion, and other minor constituents when needed.

As the carbon source, only sucrose as mentioned above may be enough. However, in the light of efficient DOI production, also, saccharides such as glucose, fructose, and molasses, organic acids such as fumaric acid, citric acid and succinic acid, alcohols such as methanol, ethanol, and glycerol, and others may be appropriately added. As the nitrogen source, there is appropriately used, an inorganic nitrogen source such as organic ammonium salt, inorganic ammonium salt, ammonia gas, or ammonia water, an organic nitrogen source such as a protein hydrolysate, or the like. As the inorganic ion, magnesium ion, phosphate ion, potassium ion, ferric ion, manganese ion, or the like is appropriately used according to need.

As organic minor constituents, there are appropriately used vitamins, amino acids, and the like, as well as yeast extracts, peptone, corn steep liquor, casein decomposition products, and others, which contain vitamins and/or amino acids.

Culture medium used in the present invention is preferably a liquid culture medium in the light of its use for industrial production.

Culture conditions vary depending on the prepared microbial mass and the culture apparatus. In general, culture temperature ranges from 20° C. to 40° C., and more preferably ranges from 25° C. to 35° C. in the light of DOI production efficiency. In addition, the pH can be set in a range from 4 to 9, preferably from 5.0 to 7.5, and more preferably from 6.0 to 7.0. The pH range can be adjusted with NaOH, $NH_3$, or the like. Culture time is not specifically limited, although it is the time necessary for the sufficient proliferation of the microbial mass and the production of DOI.

In general, culture usually uses a fermentor that can control temperature, pH, aeration conditions, and stirring speed. In the present invention, culture does not necessarily require such a fermentor. In the case of culture using a fermentor, seed culture as a preculture may be carried out in advance if necessary and the precultured cells may be inoculated in a culture medium placed in the fermentor in which a required amount of the culture medium is prepared in advance.

When DOI is produced by culturing the microorganism obtained in the present invention, no aeration may be necessary, although aeration is preferred to obtain more desirable results. Under aeration conditions implied herein, air does not necessarily need to pass through the culture solution. Depending on the shape of the fermentor, the aeration conditions include surface aeration in which an air layer above the culture solution is ventilated while the culture solution is being stirred moderately. Aeration means that an oxygen-containing gas is allowed to flow in the fermentor.

In aeration into the culture solution, dissolved oxygen concentration changes depending on the combinations of the internal pressure, the position and shape of the stirring blade, and the stirring speed. Accordingly, using as indexes the DOI productivity, the amounts of organic acids other than DOI, and the like, the optimum conditions can be obtained as follows. For example, in the case of culture using a relatively small fermentor, such as the culture apparatus BMJ-01 manufactured by ABLE Co., Ltd., when using 500 g of the culture solution, preferable results can be obtained under the aeration conditions achievable at an air flow rate of 0.005 L/min to 2 L/min under normal pressure and at a stirring speed of 50 rpm to 2000 rpm, and more preferably at an air flow rate of 0.05 L/min to 1 L/min under normal pressure and at a stirring speed of 100 rpm to 1000 rpm.

The above-mentioned aeration conditions do not need to be implemented consistently from the beginning to the end of the culture and may be implemented in a part of the culture process, whereby preferable results can be still obtained.

At the collection step, DOI obtained by the above contact is collected. In general, DOI is collected from the culture product obtained by the above-described culture.

Culture product in the present invention includes microbial mass, a culture solution, and a processed substance thereof, which are produced by the above-described method.

As the method of collecting DOI from the culture product, for example, from the culture solution, a commonly known method can be used. For example, after removing the bacterial cells by centrifugal separation, the culture supernatant is added to an ion exchange resin to elute with distilled water. With the measurements of refraction, pH, and conductivity, a fraction containing no impurity is isolated and the aqueous solution thereof is removed to collect DOI. In addition, the bacterial cell produced by the method of the present invention has produced an enzyme group appropriate for DOI production. Thus, further production and collection of DOI by using the enzyme group is also regarded as a part of the method of colleting DOI from the culture product.

The present invention can produce DOI at an extremely high level by using an inexpensive, plant-derived sugar as the raw material and is very useful for the diffusion of carbon neutral DOI.

EXAMPLES

Hereinafter, the present invention is described with reference to the following examples but is not limited thereto. Unless otherwise specifically indicated, "%" refers to "% by mass".

Example 1

Cloning of Regions near *Escherichia coli* pgi Gene

The entire base sequence of *Escherichia coli* genomic DNA is known (GenBank accession number U00096), and the base sequence of the gene encoding phosphoglucose isomerase (hereinafter may be referred to as pgi) of *Escherichia coli* has also been reported. To clone a region adjacent to the base sequence of the gene encoding pgi (1,650 bp), there were synthesized four kinds of oligonucleotide primers having the respective base sequences of CAGGAATTCG CTATATCTGG CTCTGCACG (SEQ ID NO:1), CAGTCTAGAG CAATACTCTT CTGATTTTGA G (SEQ ID NO:2), CAGTCTAGAT CATCGTCGAT ATGTAGGCC (SEQ ID NO:3), and GACCTGCAGA TCATCCGTCA GCTGTACGC (SEQ ID NO:4). The primer of SEQ ID NO:1 has an EcoRI recognition site at the 5'-terminal; the primers of SEQ ID NO:2 and SEQ ID NO:3 have an XbaI recognition site at the 5'-terminal; and the primer of SEQ ID NO:4 has a PstI recognition site at the 5'-terminal, respectively.

The genomic DNA of the *Escherichia coli* MG1655 strain was prepared according to the method described in Current Protocols in Molecular Biology (John Wiley & Sons). PCR was carried out under normal conditions using 1 μg of the prepared genomic DNA and 100 pmol of DNA of each primer described above, with a combination of the primers having the base sequences of SEQ ID NO:1 and SEQ ID NO:2, and with a combination of the primers having the base sequences of SEQ ID NO:3 and SEQ ID NO:4, respectively. Thereby, there were amplified DNA fragments of about 1.0 kb for each (hereinafter may be referred to as pgi-L fragment and pgi-R fragment, respectively). These DNA fragments were separated by agarose electrophoresis and recovered. Then, the pgi-L fragment was digested with EcoRI and XbaI, and the pgi-R fragment was digested with XbaI and PstI, respectively. These two kinds of digested fragments were mixed with a digest of the temperature-sensitive plasmid pTH18cs1 (GenBank accession number AB019610) with EcoRI and PstI, and the mixture was reacted with T4 DNA ligase, followed by transformation into *Escherichia coli* DH5alpha competent cells (manufactured by Takara Bio Inc.) to obtain a plasmid containing two fragments, namely a 5'-upstream adjacent fragment and a 3'-downstream adjacent fragment of the gene encoding pgi. The obtained plasmid was named pTHΔpgi.

Example 2

Construction of *Escherichia coli* MG1655Δpgi Strain

The plasmid pTHΔpgi obtained in Example 1 was transformed into the *Escherichia coli* MG1655 strain and cultured overnight on an LB agar plate containing 10 μg/ml of chloramphenicol at 30° C. at which cells can retain temperature-sensitive plasmid, whereby a transformant was obtained. The obtained transformant was cultured for 3 hours to overnight on an LB culture medium at 30° C., then diluted with an LB liquid culture medium or physiological saline solution, and applied onto an LB agar plate containing 10 μg/ml of chloramphenicol. The LB agar plate was cultured at 42° C. at which temperature-sensitive plasmid cannot be retained, and the grown transformant was obtained as a strain in which the entire plasmid was incorporated into the *Escherichia coli* genome by homologous recombination between exogenome and genome.

From the strain, genomic DNA was obtained and used as a template to carry out PCR. The results showed the presence of the chloramphenicol-resistant gene present in the pTH18cs1 on the genome and the presence of a region homologous to each of the region near 5'-side and the region near 3'-side of the pgi-encoding gene on the genome, whereby it was confirmed to be the strain containing the entire plasmid incorporated into the *Escherichia coli* genome.

The strain containing the entire plasmid incorporated into the *Escherichia coli* genome was seeded into a 100-ml flask equipped with baffles containing 20 ml of an LB liquid culture medium containing no chloramphenicol to be cultured under shaking condition at 30° C. for 4 hours. The resulting culture solution was diluted with an LB liquid culture medium containing no chloramphenicol and applied onto an LB agar culture medium containing no chloramphenicol. The LB agar culture medium was cultured at 42° C. to grow colonies, 96 of which were randomly selected. The colonies each were grown on an LB agar culture medium containing no chloramphenicol and on an LB agar culture medium containing chloramphenicol to select a chloramphenicol-sensitive strain.

Then, genomic DNA was prepared from the selected strain and used as a template to carry out PCR, thereby selecting a strain in which the pgi-encoding gene was deleted. The strain was named MG1655Δpgi strain.

Example 3

Cloning of Regions near *Escherichia coli* zwf Gene

The base sequence of the gene encoding glucose-6-phosphate dehydrogenase (hereinafter may be referred to as zwf) of *Escherichia coli* has also been reported. To clone a region adjacent to the base sequence of the gene encoding zwf (1,476 bp), there were synthesized four kinds of oligonucleotide primers having the respective base sequences of CAGGAATTCA TGCGTTGCAG CACGATATC (SEQ ID NO:5), CAGTCTAGAT AACCCGGTAC TTAAGCCAG (SEQ ID NO:6), CAGTCTAGAC TGCGCTTATC CTTTATGGT (SEQ ID NO:7), and GACCTGCAGT TACCGGTCAT GCGTGTAAC (SEQ ID NO:8). The primer of SEQ ID NO:5 has an EcoRI recognition site at the 5'-terminal; the primers of SEQ ID NO:6 and SEQ ID NO:7 have an XbaI recognition site at the 5'-terminal; and the primer of SEQ ID NO:8 has a PstI recognition site at the 5'-terminal, respectively.

PCR was carried out under normal conditions using 1 μg of the genomic DNA of the *Escherichia coli* MG1655 strain and 100 pmol of DNA of each primer described above, with a combination of the primers having the base sequences of SEQ ID NO:5 and SEQ ID NO:6, and with a combination of the primers having the base sequences of SEQ ID NO:7 and SEQ ID NO:8, respectively. Thereby, a DNA fragment of about 0.85 kb (hereinafter may be referred to as zwf-L fragment) and a DNA fragment of about 1.0 kb (hereinafter may be referred to as zwf-R fragment) were each amplified. These DNA fragments were separated by agarose electrophoresis and recovered. Then, the zwf-L fragment was digested with EcoRI and XbaI, and the zwf-R fragment was digested with XbaI and PstI, respectively. These two kinds of digested fragments were mixed with a digest of the temperature-sensitive plasmid pTH18cs1 with EcoRI and PstI, and the mixture was reacted with T4 DNA ligase, followed by transformation into *Escherichia coli* DH5alpha competent cells (manufactured by Takara Bio Inc.) to obtain a plasmid containing two fragments, namely a 5'-upstream adjacent fragment and a 3'-downstream adjacent fragment of the gene encoding zwf. The obtained plasmid was named pTHΔzwf.

Example 4

Construction of *Escherichia coli* MG1655ΔpgiΔzwf Strain

The plasmid pTHΔzwf obtained in Example 3 was transformed into the *Escherichia coli* MG1655Δpgi strain obtained in Example 2 and cultured overnight on an LB agar plate containing 10 µg/ml of chloramphenicol at 30° C. at which cells can retain temperature-sensitive plasmid, whereby a transformant was obtained. The obtained transformant was cultured for 3 hours to overnight on an LB culture medium at 30° C., then diluted with an LB liquid culture medium or physiological saline solution, and applied onto an LB agar plate containing 10 µg/ml of chloramphenicol. The LB agar plate was cultured at 42° C. at which temperature-sensitive plasmids cannot be retained, and the grown transformant was obtained as a strain in which the entire plasmid was incorporated into the *Escherichia coli* genome by homologous recombination between exogenome and genome.

From the strain, genomic DNA was obtained and used as a template to carry out PCR. The results showed the presence of the chloramphenicol-resistant gene present in the pTH18cs1 on the genome and the presence of a region homologous to each of the region near 5'-side and the region near 3'-side of the zwf-encoding gene on the genome, whereby it was confirmed to be the strain containing the entire plasmid incorporated into the *Escherichia coli* genome.

The strain containing the entire plasmid incorporated into the *Escherichia coli* genome was seeded into a 100-ml flask equipped with baffles containing 20 ml of an LB liquid culture medium containing no chloramphenicol to be cultured under shaking condition at 30° C. for 4 hours. The resulting culture solution was diluted with an LB liquid culture medium containing no chloramphenicol and applied onto an LB agar culture medium containing no chloramphenicol. The LB agar culture medium was cultured at 42° C. to grow colonies, 96 of which were randomly selected. The colonies each were grown on an LB agar culture medium containing no chloramphenicol and on an LB agar culture medium containing chloramphenicol to select a chloramphenicol-sensitive strain.

Then, genomic DNA was prepared from the selected strain and used as a template to carry out PCR, thereby selecting a strain in which the zwf-encoding gene was deleted. The strain was named MG1655ΔpgiΔzwf strain.

Example 5

Construction of Expression Vector of DOI Synthase Gene (btrC) Under Control of GAPDH Promoter The base sequence of the GAPDH gene of *Escherichia coli* has already been reported. To obtain a glyceraldehyde-3-phosphate dehydrogenase (GAPDH) promoter, there were synthesized respective oligonucleotide primers having the respective base sequences of CGAGCTACAT ATGCAAT-GAT TGACACGATT CCG (SEQ ID NO:9) and CCAAGCT-TCT GCAGGTCGAC GGATCCGAGC TCAGCTATTT GTTAGTGAAT AAAAGG (SEQ ID NO:10). The primer of SEQ ID NO:9 has a NdeI recognition site at the 5'-terminal; and the primer of SEQ ID NO:10 sequentially has HindIII, PstI, SalI, BamHI, and SacI recognition sites from the 5'-terminal.

Along with the above two kinds of primers, the genomic DNA of the *Escherichia coli* MG1655 strain was used as a template to carry out PCR under normal conditions, thereby amplifying a DNA fragment. The obtained DNA fragment was digested with restriction enzymes NdeI and HindIII to obtain a GAPDH promoter-encoding fragment of about 100 bp. Next, the above DNA fragment was mixed with pBR322 (GenBank accession number J01749) digested with NdeI and HindIII as a cloning vector for *Escherichia coli*, ligated using a ligase, and then transformed into *Escherichia coli* DH5alpha competent cells (manufactured by Takara Bio Inc.) to obtain a transformant grown on an LB agar plate containing 50 µg/mL of ampicillin. The obtained colonies were cultured overnight on an LB liquid culture medium containing 50 µg/mL of ampicillin at 30° C. to recover a plasmid from the obtained bacterial cell. The plasmid was named pGAP.

The base sequence of the DOI synthase gene (btrC) present in *Bacillus circulans* (ATCC 4513) has already been reported (GenBank accession number AB066276). To obtain the btrC gene, there were synthesized respective oligonucleotide primers having the respective base sequences of CACTG-GAGCT CGCTGGTGGA ATATATGACG ACTAAACAAA TTTG (SEQ ID NO:11) and CAGGATCCTT ACAGC-CCTTC CCGGATC (SEQ ID NO:12). The primer of SEQ ID NO:11 sequentially has a SacI recognition site and a 13 base-long ribosome binding sequence of the GAPDH gene from the 5'-terminal. The primer of SEQ ID NO:12 has a BamHI recognition site at the 5'-terminal.

Along with the above two kinds of primers, the genomic DNA of *Bacillus circulans* was used as a template to carry out PCR under normal conditions, and the obtained DNA fragment was digested with restriction enzymes SacI and BamHI to obtain a DOI synthase gene (btrC) fragment of about 1.1 kbp. This DNA fragment was mixed with a fragment obtained by digesting the plasmid pGAP with restriction enzymes SacI and BamHI, ligated using a ligase, and then transformed into *Escherichia coli* DH5alpha competent cells (manufactured by Takara Bio Inc.) to obtain a transformant grown on an LB agar plate containing 50 µg/mL of ampicillin. The obtained colonies were cultured overnight on an LB liquid culture medium containing 50 µg/mL of ampicillin at 30° C. to recover a plasmid pGAP-btrC from the obtained bacterial cell, thereby constructing a DOI synthase gene (btrC)-expressing vector.

Example 6

Construction of Expression Vector of DOI Synthase Gene (btrC) and Sucrose Hydrolase Gene (cscA) Under Control of GAPDH Promoter The base sequence of the sucrose hydrolase gene (cscA) present in the *Escherichia coli* O157 strain has already been reported. Namely, it is shown in 3274383-3275816 of the *Escherichia coli* O157 strain genome sequence described by GenBank accession number AE005174. To obtain the cscA gene, there were synthesized respective oligonucleotide primers having the respective base sequences of GCGGATC-CGC TGGTGGAATA TATGACGCAA TCTCGATTGC (SEQ ID NO:13) and GACGCGTCGA CTTAACCCAG TTGCCAGAGT GC (SEQ ID NO:14). The primer of SEQ ID NO:13 sequentially has a BamHI recognition site and a 13 base-long ribosome binding sequence of the GAPDH gene from the 5'-terminal. The primer of SEQ ID NO:14 has a SalI recognition site at the 5'-terminal.

Along with the above two kinds of primers, the genomic DNA of the *Escherichia coli* O157 strain (IRMM449: Sigma-Aldrich Corp.) was used as a template to carry out PCR under normal conditions, and the obtained DNA fragment was digested with restriction enzymes BamHI and SalI to obtain a sucrose hydrolase gene (cscA) fragment of about 1.4 kbp. This DNA fragment was mixed with a fragment obtained by digesting the plasmid pGAP-btrC with restriction enzymes BamHI and SacI, ligated using a ligase, and then transformed into *Escherichia coli* DH5alpha competent cells (manufactured by Takara Bio Inc.) to obtain a transformant grown on an LB agar plate containing 50 μg/mL of ampicillin. The obtained colonies were cultured overnight on an LB liquid culture medium containing 50 μg/mL of ampicillin at 30° C. to recover a plasmid pGAP-btrC-cscA from the obtained bacterial cell, thereby constructing a vector expressing the DOI synthase gene (btrC) and the sucrose hydrolase gene (cscA).

Example 7

Construction of Expression Vector of DOI Synthase Gene (btrC), Sucrose Hydrolase Gene (cscA), and Glucose Transport Facilitator Gene (Glf) Under Control of GAPDH Promoter The base sequence of the glucose transport facilitator gene (glf) present in *Zymomonas mobilis* (ATCC 29191) has already been reported (GenBank accession number M60615). To obtain the glf gene, there were synthesized respective oligonucleotide primers having the respective base sequences of CCTGTCGACG CTGGTGGAAT ATAT-GAGTTC TGAAAGTAGT CAGG (SEQ ID NO:15) and CTACTGCAGC TACTTCTGGG AGCGCCACA (SEQ ID NO:16). The primer of SEQ ID NO:15 sequentially has a SalI recognition site and a 13 base-long ribosome binding sequence of the GAPDH gene from the 5'-terminal. The primer of SEQ ID NO:16 has a PstI recognition site at the 5'-terminal.

Along with the above two kinds of primers, the genomic DNA of *Zymomonas mobilis* was used as a template to carry out PCR under normal conditions, and the obtained DNA fragment was digested with restriction enzymes SalI and PstI to obtain a glucose transport facilitator gene (glf) fragment of about 1.4 kbp. This DNA fragment was mixed with a fragment obtained by digesting the plasmid pGAP-btrC-cscA with restriction enzymes SalI and PstI, ligated using a ligase, and then transformed into *Escherichia coli* DH5alpha competent cells (manufactured by Takara Bio Inc.) to obtain a transformant grown on an LB agar plate containing 50 μg/mL of ampicillin. The obtained colonies were cultured overnight on an LB liquid culture medium containing 50 μg/mL of ampicillin at 30° C. to recover a plasmid pGAP-btrC-cscA-glf from the obtained bacterial cell, thereby constructing a vector expressing the DOI synthase gene (btrC), the sucrose hydrolase gene (cscA), and the glucose transport facilitator gene (glf).

Example 8

Introduction of pGAP-btrC-cscA and pGAP-btrC-cscA-Glf into MG1655ΔPgiΔZwf Strain The above plasmids pGAP-btrC-cscA and pGAP-btrC-cscA-glf were each transformed into the MG1655ΔpgiΔzwf strain and cultured overnight on an LB agar plate containing 50 μg/mL of ampicillin at 37° C. to obtain an MG1655ΔpgiΔzwf/pGAP-btrC-cscA strain and an MG1655ΔpgiΔzwf/pGAP-btrC-cscA-glf strain.

Example 9

DOI Productivity by MG1655ΔPgiΔZwf/pGAP-btrC-cscA Strain and Difference DOI Productivity by Culture pH As a preculture, the *Escherichia coli* MG1655ΔpgiΔzwf/pGAP-btrC-cscA strain was seeded into an Erlenmeyer flask containing 25 mL of an LB Broth, Miller culture solution (Difco244620) and cultured with stirring at 120 rpm overnight. Then, all amount of the resulting product was seeded into a 1 L-working volume fermentor (the culture apparatus BMJ-01 manufactured by ABLE Co., Ltd.) containing 475 g of a culture medium having a composition shown below. The culture was performed under atmospheric pressure, at an air flow rate of 1.0 vvm, at a stirring speed of 800 rpm, and at a culture temperature of 30° C. Four fermentors in total were used, in which the pH was adjusted to 7.0, 6.5, and 6.0 using 12.5% ammonia water and 2N hydrochloric acid. In addition, by measuring absorbance at 660 nm, the bacterial cell concentration was measured. At the beginning of culture, the bacterial cell concentration was all 0.29. After 62 hours in culture, the amounts of DOI, sucrose, glucose, and fructose contained in the obtained culture solution were measured according to the usual method by HPLC. Also, the bacterial cell concentration was measured by measuring absorbance at 660 nm. Table 1 below shows the composition of the culture medium used for the culture. Table 2 shows the results.

TABLE 1

| Sucrose | 10.0% |
|---|---|
| Yeast extract | 1.0% |
| Bacto tryptone | 1.6% |
| Sodium chloride | 0.5% |

TABLE 2

| pH | 7.0 | 6.5 | 6.0 |
|---|---|---|---|
| Culture time (hr) | 62 | 62 | 62 |
| Bacterial cell concentration (OD660 value) | 42.3 | 39.4 | 35.0 |
| Amount of DOI accumulated (g/L) | 31 | 36 | 33 |
| Sucrose (g/L) | 0 | 0 | 0 |
| Glucose (g/L) | 14 | 15 | 15 |
| Fructose (g/L) | 40 | 18 | 18 |

By the present Example, it was confirmed that DOI can be produced from sucrose using the *Escherichia coli* MG1655ΔpgiΔzwf/pGAP-btrC-cscA strain.

In the bacterium used in the present Example, since the pgi gene and the zwf gene were simultaneously disrupted, the catabolism of glucose was supposed to be impossible. However, as the result of the 62-hour culture in the culture medium using sucrose as the only carbon source, the amount of the bacterium increased 100-fold or more in all test sections. Thereby, it was confirmed that the *Escherichia coli* of the present invention does not require expensive mannitol for the proliferation and growth of the bacterial cell and uses fructose obtained by decomposing sucrose for the proliferation and growth thereof.

When the pH was changed to 7.0, 6.5, and 6.0, the amount of DOI accumulated was 31 g/L, 36 g/L, and 33 g/L, where the accumulation amount was the largest at the pH of 6.5. After 62 hours in culture, the added sucrose was completely decomposed under all of the pH conditions, and the amount of fructose in the culture medium was the smallest at the pH of 6.5 or lower. This indicated that, at the pH of 6.5 or lower, fructose obtained by the decomposition of sucrose was most efficiently incorporated in the bacterial cell. At the pH of 6.5 or lower, fructose uptake was faster than at the pH of 7.0 despite the presence of glucose still remaining in the culture medium. Thus, obviously, the DOI-producing *Escherichia coli* efficiently incorporates glucose and fructose thereinto.

Example 10

DOI Production by
MG1655ΔpgiΔzwf/pGAP-btrC-cscA Strain and
MG1655ΔpgiΔzwf/pGAP-btrC-cscA-glf Strain As a preculture, the *Escherichia coli* MG1655ΔpgiΔzwf/pGAP-btrC-cscA strain and MG1655ΔpgiΔzwf/pGAP-btrC-cscA-glf strain were each seeded into an Erlenmeyer flask containing 25 ml of LB Broth, Miller culture solution (Difco244620) and cultured with stirring at 120 rpm overnight. Then, all amount of the each resulting product was seeded into a 1 L-working volume fermentor (the culture apparatus BMJ-01 manufactured by ABLE Co., Ltd.) containing 475 g of a culture medium having a composition shown below. The culture was performed under atmospheric pressure, at the air flow rate of 1.0 vvm, at the stirring speed of 800 rpm, at the culture temperature of 30° C., and at the pH of 6.5 (adjusted with 12.5% ammonia water). After 48 hours in culture, the amounts of DOI, sucrose, and glucose in the obtained culture solution were measured according to the usual method by HPLC. Table 3 below shows the composition of the culture medium used for the culture. Table 4 shows the results.

TABLE 3

| Sucrose | 10.0% |
|---|---|
| Yeast extract | 1.0% |
| Bacto tryptone | 1.6% |
| Sodium chloride | 0.5% |

TABLE 4

| Expression vector | pGAP-btrC-cscA | pGAP-btrC-cscA-glf |
|---|---|---|
| Culture time (hr) | 48 | 48 |
| Amount of DOI accumulated (g/L) | 31 | 44 |
| Sucrose (g/L) | 0 | 0 |
| Glucose (g/L) | 25 | 0 |

After 48 hours in culture, in the MG1655ΔpgiΔzwf/pGAP-btrC-cscA strain, 31 g/L of DOI was confirmed to be accumulated, and in the MG1655ΔpgiΔzwf/pGAP-btrC-cscA-glf strain, 44 g/L of DOI was confirmed to be accumulated. The results of the present Example show that the introduction of the glf gene improves the productivity of DOI. In the results of the Example, in all the strains, sucrose added at the beginning of the culture was completely consumed. It was also suggested that, in the strain containing the introduced glf gene, glucose consumption was obviously faster than in the strain containing no introduced glf gene, and glucose was efficiently converted to DOI by providing the Glf activity.

Example 11

DOI Production from Sucrose by Using Industrial
Culture Medium with
BΔpgiΔzwf/pGAP-btrC-cscA-glf Strain and
MG1655ΔpgiΔzwf/pGAP-btrC-cscA-glf Strain In general, industrial production employs corn steep liquor instead of yeast extract and the like expensive as culture medium components. The productivity of DOI by using a corn steep liquor culture medium was compared between the MG1655 strain and the B strain, which are subspecies of *Escherichia coli*.

In the *Escherichia coli* B strain (ATCC 11303), similarly, the methods described in Examples 1 to 4 were used to disrupt the pgi gene and the zwf gene, and the obtained strain was named BΔpgiΔzwf strain. Into the strain obtained, the expression vector pGAP-btrC-cscA-glf was introduced by the method described in Example 8 and the obtained bacterium was named BΔpgiΔzwf/pGAP-btrC-cscA-glf strain.

As a preculture, the BΔpgiΔzwf/pGAP-btrC-cscA-glf strain and the MG1655ΔpgiΔzwf/pGAP-btrC-cscA-glf strain were each seeded into an Erlenmeyer flask containing 25 mL of an LB Broth, Miller culture solution (Difco244620) and cultured with stirring at 120 rpm overnight. Then, all amount of the each resulting product was seeded into a 1 L-working volume fermentor (the culture apparatus BMJ-01 manufactured by ABLE Co., Ltd.) containing 475 g of a culture medium having a composition shown below. The culture was performed under atmospheric pressure, at an air flow rate of 1.5 vvm, at the stirring speed of 800 rpm, at the culture temperature of 30° C., and at a pH of 6.2 (adjusted with 12.5% ammonia water). As a fermentation raw material, a 50% sucrose solution was added at a speed of 4 g/hour during the culture. The amount of DOI contained in the obtained culture solution was measured according to the usual method by HPLC. Table 5 below shows the composition of the culture medium used for the culture. Table 6 and FIG. 1 show the results. In Table 6, "–" represents that there was no measured value. In FIG. 1, the black circles represent the BΔpgiΔzwf/pGAP-btrC-cscA-glf strain and the white squares represent the MG1655ΔpgiΔzwf/pGAP-btrC-cscA-glf strain.

TABLE 5

| Corn steep liquor | 3.0% |
|---|---|
| Dipotassium hydrogen phosphate | 0.2% |
| Potassium dihydrogen phosphate | 0.2% |
| Ammonium sulfate | 0.2% |
| Magnesium sulfate heptahydrate | 0.2% |
| Ferrous sulfate heptahydrate | 0.01% |

TABLE 6

| Strain | BΔpgiΔzwf/pGAP-btrC-cscA-glf strain | MG1655ΔpgiΔzwf/pGAP-btrC-cscA-glf strain |
|---|---|---|
| After 0 hours | 0.0 g/L | 0.0 g/L |
| After 3 hours | 0.0 g/L | — |
| After 24 hours | 15.4 g/L | 10.0 g/L |
| After 30 hours | 21.2 g/L | — |
| After 48 hours | 38.5 g/L | 9.8 g/L |

After 48 hours in culture, in the BΔpgiΔzwf/pGAP-btrC-cscA-glf strain, 38.5 g/L of DOI was confirmed to be accumulated, and in the MG1655ΔpgiΔzwf/pGAP-btrC-cscA-glf strain, 9.8 g/L of DOI was confirmed to be accumulated. The results of the present Example indicated that using the *Escherichia coli* B strain extremely improved the productivity of DOI as compared with the MG1655 strain.

Example 12

DOI Production from Blackstrap Molasses by
BΔpgiΔzwf/pGAP-btrC-cscA Strain,
BΔpgiΔzwf/pGAP-btrC-cscA-glf Strain, and
BΔpgiΔzwf/pGAP-btrC-cscA-pck Strain As a glucose transport facilitator gene other than the glf gene, phosphoenolpyruvate carboxykinase (Pck) was selected. Phosphoenolpyruvate carboxykinase (Pck) is a protein that produces phosphoenolpyruvate with oxaloacetic acid as a substrate. The glucose uptake system (PTS) inherent in *Escherichia coli* requires phosphoenolpyruvate. Accordingly, it is expected that the high expression of the protein can increase the amount of phosphoenolpyruvate supplied, resulting in the enhancement of the PTS.

The base sequence of phosphoenolpyruvate carboxykinase (Pck) present in *Escherichia coli* has already been reported (GenBank accession number M59823). To obtain the pck gene, there were prepared respective primers having the respective base sequences of TACTGCAGAG CTGGTGGAAT ATATGCGCGT TAACAATGGT TTG (SEQ ID NO:17) and TACTGCAGTT ACAGTTTCGG ACCAGCCG (SEQ ID NO:18). The primer of SEQ ID NO:17 sequentially has a PRI recognition site and a 13 base-long ribosome binding sequence of the GAPDH gene from the 5'-terminal. The primer of SEQ ID NO:18 has a PstI recognition site at the 5'-terminal. Along with the above two kinds of primers, the genomic DNA of the *Escherichia coli* B strain was used as a template to carry out PCR under normal conditions, and the obtained DNA fragment was digested with restriction enzyme PstI to obtain a phosphoenolpyruvate carboxykinase gene (pck) fragment of about 1.6 kbp. This DNA fragment was mixed with a fragment obtained by digesting the plasmid pGAP-btrC-cscA with restriction enzyme PstI, ligated using a ligase, and then transformed into *Escherichia coli* DH5alpha competent cells (manufactured by Takara Bio Inc.) to obtain a transformant grown on an LB agar plate containing 50 μg/mL of ampicillin. The obtained colonies were cultured overnight on an LB liquid culture medium containing 50 μg/mL of ampicillin at 30° C. to recover a plasmid pGAP-btrC-cscA-pck from the obtained bacterial cell, thereby constructing a vector expressing the DOI synthase gene (btrC), the sucrose hydrolase gene (cscA), and the phosphoenolpyruvate carboxykinase gene (pck).

The expression vector pGAP-btrC-cscA-pck was introduced into the BΔpgiΔzwf strain by the method described in Example 8 to name it BΔpgiΔzwf/pGAP-btrC-cscA-pck.

Figure 2:
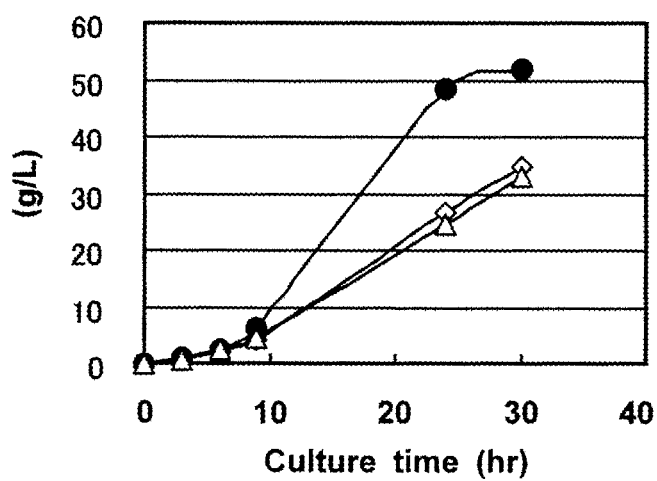
FIG. 2 shows a chart indicating the DOI productivities of bacterial strains obtained in Example 12 of the present invention.

As a preculture, the BΔpgiΔzwf/pGAP-btrC-cscA strain, the BΔpgiΔzwf/pGAP-btrC-cscA-glf strain, and the BΔpgiΔzwf/pGAP-btrC-cscA-pck strain were each seeded into an Erlenmeyer flask containing 25 mL of LB Broth, Miller culture solution (Difco244620) and cultured with stirring at 120 rpm overnight. Then, all amount of the each resulting product was seeded into a 1 L-working volume fermentor (the culture apparatus BMJ-01 manufactured by ABLE Co., Ltd.) containing 475 g of a culture medium having a composition shown below. The culture was performed under atmospheric pressure, at an air flow rate of 2.0 vvm, at a stirring speed of 1000 rpm, at a culture temperature of 32° C., and at the pH of 6.2 (adjusted with 12.5% ammonia water). As a fermentation raw material, a 90% blackstrap molasses solution was added at a speed of 6 g/hour during the culture. The amount of DOI contained in the obtained culture solution was measured according to the usual method by HPLC. Table 7 below shows the composition of the culture medium used for the culture. Table 8 and FIG. 2 show the results. In FIG. 2, the white rhombuses represent the BΔpgiΔzwf/pGAP-btrC-cscA strain, the black circles represent the BΔpgiΔzwf/pGAP-btrC-cscA-glf strain, and the white triangles represent the BΔpgiΔzwf/pGAP-btrC-cscA-pck strain.

TABLE 7

| Corn steep liquor | 1.0% |
|---|---|
| Dipotassium hydrogen phosphate | 0.2% |
| Potassium dihydrogen phosphate | 0.2% |
| Ammonium sulfate | 0.2% |
| Magnesium sulfate heptahydrate | 0.2% |
| Ferrous sulfate heptahydrate | 0.01% |

TABLE 8

| Strain | BΔpgiΔzwf/ pGAP-btrC- cscA Strain | BΔpgiΔzwf/ pGAP-btrC-cscA- glf strain | BΔpgiΔzwf/ pGAP-btrC-cscA- pck strain |
|---|---|---|---|
| After 0 hours | 0.0 g/L | 0.0 g/L | 0.0 g/L |
| After 3 hours | 0.9 g/L | 0.9 g/L | 0.9 g/L |
| After 6 hours | 2.3 g/L | 2.5 g/L | 2.4 g/L |
| After 9 hours | 4.4 g/L | 6.4 g/L | 4.6 g/L |
| After 24 hours | 26.8 g/L | 48.3 g/L | 24.7 g/L |
| After 30 hours | 34.8 g/L | 51.9 g/L | 32.8 g/L |

After 30 hours in culture, in the BΔpgiΔzwf/pGAP-btrC-cscA strain, 34.8 g/L of DOI accumulation was found; in the BΔpgiΔzwf/pGAP-btrC-cscA-glf strain, 51.9 g/L of DOI accumulation was found; and in the BΔpgiΔzwf/pGAP-btrC-cscA-pck strain, 32.8 g/L of DOI accumulation was found. The results of the present Example showed that the productivity of DOI obtained by introducing the pck gene was almost the same as that obtained without introducing the pck gene, which thus indicated that Pck does not increase the productivity of DOI. Therefore, it was found that, to improve the productivity of DOI, providing the Glf activity by the introduction of the glf gene is much more effective than enhancing the glucose uptake system (PTS) inherent in *Escherichia coli*.

Comparative Example 1

To investigate the effect of introduction of the glf gene on the production of a substance other than DOI, the cscA gene and the glf gene were introduced into an MG1655ΔpflΔdldΔmdhΔasp/GAPldhA genome-inserted strain, which is a D-lactic acid-producing bacterium to study the amounts of lactic acid produced.

The MG1655ΔpflΔdldΔmdhΔasp/GAPldhA genome-inserted strain is a strain in which genes encoding pyruvate formate-lyase (Pfl), FAD-dependent D-lactic acid dehydrogenase (Dld), malate dehydrogenase (Mdh), and aspartate ammonia-lyase (Asp) have been disrupted and a gene encoding NADH-dependent D-lactate dehydrogenase (LdhA) has been introduced. WO No. 2005/033324 has confirmed that the strain produced 98 g/L of D-lactic acid from 120 g of glucose.

<Construction of Expression Vector of *Escherichia coli* O157-Derived Sucrose Hydrolase Gene (cscA), Construction of Expression Vector of *Escherichia coli* O157-Derived Sucrose Hydrolase Gene (cscA) and *Zymomonas mobilis*-Derived Glucose Transport Facilitator Gene (glf), and Construction of Transformants of the Expression Vectors>

The base sequence of the GAPDH gene of *Escherichia coli* has already been reported. To obtain a glyceraldehyde-3-phosphate dehydrogenase (GAPDH) promoter, there were synthesized the respective primers having the respective base sequences of SEQ ID NO:9 and SEQ ID NO:10. The primer of SEQ ID NO:9 has a NdeI recognition site at the 5'-terminal; and the primer of SEQ ID NO:10 sequentially has HindIII, PstI, SalI, BamHI, and SacI recognition sites from the 5'-terminal.

Along with the above two kinds of primers, the genomic DNA of the *Escherichia coli* MG1655 strain was used as a template to carry out PCR under normal conditions, thereby amplifying a DNA fragment. The obtained DNA fragment was digested with restriction enzymes NdeI and HindIII to obtain a GAPDH promoter-encoding fragment of about 100 bp. Next, the above DNA fragment was mixed with pBR322 (GenBank accession number J01749) digested with NdeI and HindIII as a cloning vector for *Escherichia coli*, ligated using a ligase, and then transformed into *Escherichia coli* DH5alpha competent cells (manufactured by Takara Bio Inc.) to obtain a transformant grown on an LB agar plate containing 50 μg/mL of ampicillin. The obtained colonies were cultured overnight on an LB liquid culture medium containing 50 μg/mL of ampicillin at 30° C. to recover a plasmid from the obtained bacterial cell. The plasmid was named pGAP.

The base sequence of the sucrose hydrolase gene (cscA) present in the *Escherichia coli* O157 strain has already been reported. Namely, it is shown in 3274383-3275816 of the *Escherichia coli* O157 strain genome sequence described by GenBank accession number AE005174. To obtain the cscA gene, there were synthesized the respective primers having the respective base sequences of SEQ ID NO:13 and SEQ ID NO:14. The primer of SEQ ID NO:13 sequentially has a BamHI recognition site and a 13 base-long ribosome binding sequence of the GAPDH gene from the 5'-terminal. The primer of SEQ ID NO:14 has a SalI recognition site at the 5'-terminal.

Along with the above two kinds of primers, the genomic DNA of the *Escherichia coli* O157 strain (IRMM449: Sigma-Aldrich Corp.) was used as a template to carry out PCR under normal conditions, and the obtained DNA fragment was digested with restriction enzymes BamHI and SalI to obtain a sucrose hydrolase gene (cscA) fragment of about 1.4 kbp. This DNA fragment was mixed with a fragment obtained by digesting the plasmid pGAP with restriction enzymes BamHI and SalI, ligated using a ligase, and then transformed into *Escherichia coli* DH5alpha competent cells (manufactured by Takara Bio Inc.) to obtain a transformant grown on an LB agar plate containing 50 μg/mL of ampicillin. The obtained colonies were cultured overnight on an LB liquid culture medium containing 50 μg/mL of ampicillin at 30° C. to recover a plasmid pGAP-cscA from the obtained bacterial cell, thereby constructing a vector expressing sucrose hydrolase gene (cscA).

The base sequence of the glucose transport facilitator gene (glf) present in *Zymomonas mobilis* (ATCC 29191) has already been reported (GenBank accession number M60615). To obtain the glf gene, there were prepared the respective primers having the respective base sequences of SEQ ID NO:15 and SEQ ID NO:16. The primer of SEQ ID NO:15 sequentially has a SalI recognition site and a 13 base-long ribosome binding sequence of the GAPDH gene from the 5'-terminal. The primer of SEQ ID NO:16 has a PstI recognition site at the 5'-terminal.

Along with the above two kinds of primers, the genomic DNA of *Zymomonas mobilis* was used as a template to carry out PCR under normal conditions, and the obtained DNA fragment was digested with restriction enzymes SalI and PstI to obtain a glucose transport facilitator gene (glf) fragment of about 1.4 kbp. This DNA fragment was mixed with a fragment obtained by digesting the plasmid pGAP-cscA with restriction enzymes SalI and PstI, ligated using a ligase, and then transformed into *Escherichia coli* DH5alpha competent cells (manufactured by Takara Bio Inc.) to obtain a transformant grown on an LB agar plate containing 50 μg/mL of ampicillin. The obtained colonies were cultured overnight on an LB liquid culture medium containing 50 μg/mL of ampicillin at 30° C. to recover a plasmid pGAP-cscA-glf from the obtained bacterial cell, thereby constructing a vector expressing the sucrose hydrolase gene (cscA) and the glucose transport facilitator gene (glf).

The above plasmids pGAP-cscA and pGAP-cscA-glf were each transformed into the MG1655ΔpflΔdldΔmdhΔasp/GAPldhA genome-inserted strain competent cells described in the patent literature WO No. 2005/033324 and cultured overnight on an LB Broth, Miller agar plate containing 50 μg/mL of ampicillin at 37° C. to obtain an MG1655ΔpflΔdldΔmdhΔasp/GAPldhA genome-inserted strain/pGAP-cscA strain and an MG1655ΔpflΔdldΔmdhΔasp/GAPldhA genome-inserted strain/pGAP-cscA-glf strain.

<D-Lactic Acid Production by MG1655ΔpflΔdldΔmdhΔasp/pGAP-cscA Strain and MG1655ΔpflΔdldΔmdhΔasp/pGAP-cscA-glf Strain>

As a preculture, 20 mL of LB Broth, Miller culture solution (Difco244620) containing 50 μg/mL of ampicillin was placed in an Erlenmeyer flask, into which the *Escherichia coli* MG1655ΔpflΔdldΔmdhΔasp/pGAP-cscA strain and MG1655ΔpflΔdldΔmdhΔasp/pGAP-cscA-glf strain were each seeded and cultured with stirring at 200 rpm for 9 hours at 30° C. Then, 0.2 mL of the preculture solution (n=4) was seeded into a 100 mL-working volume flask containing 20 mL of a culture medium having a composition shown below to culture at a stirring speed of 90 rpm and at a culture temperature of 35° C. Table 9 below shows the composition of the culture medium used for the culture. Sucrose was used after filter sterilization. The fixed quantities of D-lactic acid and sucrose in the obtained culture solution were determined according to the usual method by HPLC. Table 10 shows the results.

TABLE 9

| Culture medium composition (in 20-mL pure water) | |
| --- | --- |
| Sucrose | 10.0% |
| Corn steep liquor | 5.0% |

Into the above culture medium 20 mL was added 10 g of calcium carbonate.

TABLE 10

| Expression vector | MG1655ΔpflΔdldΔmdhΔasp/pGAP-cscA | MG1655ΔpflΔdldΔmdhΔasp/pGAP-cscA-glf |
| --- | --- | --- |
| Culture time (hr) | 42 | 42 |
| Amount of lactic acid accumulated (g/L) | 41 ± 11 | 7.9 ± 2 |
| Sucrose (g/L) | 0 | 0 |

As shown in Table 10, the productivity of D-lactic acid using the MG1655ΔpflΔdldΔmdhΔasp/pGAP-cscA-glf strain was lower than that using the MG1655ΔpflΔdldΔmdhΔasp/pGAP-cscA strain. In the D-lactic acid-producing *Escherichia coli*, there was found no effect of introduction of the glf gene on productivity improvement, and the rather negative effect was shown. This indicates that the introduction of the glf gene does not necessarily increase the amount of a substance produced in its production process by fermentation.

The entire disclosure of Japanese Patent Application No. 2008-284639 filed on Nov. 5, 2008 is hereby incorporated by reference herein in its entirety.

All the literature, patent applications, and technical standards described herein are incorporated herein by reference to the same extent as in cases where each literature, patent application, or technical standard is specifically and individually described to be incorporated by reference.

The invention claimed is:

1. A 2-deoxy-scyllo-inosose (DOI)-producing *Escherichia coli*, which is provided with a DOI production system or has an enhanced DOI production system by introducing a DOI synthase (BtrC)-encoding gene derived from *Bacillus circulans* into a host, wherein a phosphoglucose isomerase (Pgi)-encoding gene and a glucose-6-phosphate-1-dehydrogenase (Zwf)-encoding gene of the host are disrupted, and only a sucrose hydrolase (CscA)-encoding gene derived from *Escherichia coli* from the gene group consisting of a repressor protein (CscR)-encoding gene, a sucrose hydrolase (CscA)-encoding gene, a fructokinase (CscK)-encoding gene, and a sucrose permease (CscB)-encoding gene is introduced into the *Escherichia coli* to provide only CscA activity from the group consisting of CscR activity, CscA activity, CscK activity, and CscB activity.

2. The DOI-producing *Escherichia coli* according to claim 1, wherein the sucrose hydrolase (CscA)-encoding gene is derived from *Escherichia coli* O157 bacteria.

3. The DOI-producing *Escherichia coli* according to claim 1, further comprising an enhanced glucose transport facilitator activity by introducing a glucose transport facilitator (Glf) gene derived from bacteria belonging to the genus *Zymomonas*.

4. The DOI-producing *Escherichia coli* according to claim 3, wherein the bacteria belonging to the genus *Zymomonas* is *Zymomonas mobilis* bacteria.

5. The DOI-producing *Escherichia coli* according to claim 1, which is a B strain or a derivative thereof.

6. A method of producing DOI, from a plant-derived raw material containing sucrose by culturing the DOI-producing *Escherichia coli* according to claim 1 in a medium comprising the plant-derived raw material containing sucrose.

* * * * *